United States Patent [19]

Mikkelsen

[11] Patent Number: Plant 6,097

[45] Date of Patent: Feb. 2, 1988

[54] POINSETTIA PLANT NAMED MERRIMAKER

[75] Inventor: James C. Mikkelsen, Ashtabula, Ohio

[73] Assignee: Mikkelsens, Inc., Ashtabula, Ohio

[21] Appl. No.: 818,801

[22] Filed: Jan. 14, 1986

[51] Int. Cl.[4] ..... A01H 5/00

[52] U.S. Cl. ..... Plt./86

[58] Field of Search ..... Plt./86

*Primary Examiner*—James R. Feyrer

*Attorney, Agent, or Firm*—Schwartz, Jeffery, Schwaab, Mack, Blumenthal & Evans

[57] ABSTRACT

A poinsettia plant named Merrimaker particularly characterized by the combined characteristics of deep bright red colored bracts, dark green foliage, strong, vigorous, upright growth, early flowering, outstanding keeping quality, and by its commercially significant ability of being grown as a single stem or pinched plant.

1 Drawing Figure

The present invention relates to a new and distinctive cultivar of poinsettia plant known by the cultivar name Merrimaker, and botanically known as *Euphoriba pulcherrima*.

Merrimaker was developed by me through controlled breeding by crossing Mikkelsen Seedling No. 72-143-2. (seed parent)×Mikkelsen Seedling No. 71-241-1 (pollen parent). Merrimaker was given the breeding number 77-63-10.

Merrimaker has been asexually reproduced by me by cuttings in the greenhouses of Mikkelsens Inc., Ashtabula, Ohio, and has been found to retain its distinctive characteristics through successive propagations.

The following characteristics distinguish the new cultivar from its parents and from other poinsettias commercially known and used in the floriculture industry:

1. Bract color is a deeper, more intense red than Paul Mikkelsen, disclosed in U.S. Plant Pat. No. 2,328, the patented cultivars Hegg Brilliant and Gottbiers V14 Glory, and the unpatented cultivar Super Rochford.

2. The involucre has many more bracts in it than Hegg Brilliant, Super Rochford, Improved Rochford (not patented), and Glory. It is larger in diameter than the involucre of Improved Rochford and Hegg Brilliant but nearly equal in size to Super Rochford and Glory.

3. Merrimaker has darker foliage than Glory but is similar in green color to the Hegg and Rochford types.

4. The flower cluster (cyathias) remains tight and does not split or spread open as does the Paul Mikkelsen, Heggs and Rochfords. Glory has a smaller compact cluster of cyathia.

5. Bract shape is more oval while the Hegg and Rochfords are more ovate in shape, and Glory is very pointed at the end of the bract compared to the other cultivars mentioned.

6. Under natural short days in Ohio, Merrimaker developed bracts and shed pollen three weeks earlier than Glory, Heggs or Rochfords. Under controlled day length using blackout cloth, all cultivars flowered nearly the same, indicating Merrimaker initiates flowers on a longer critical natural day length.

7. Cyathias are retained longer than the other cultivars, and Merrimaker tolerates lower light stress, both higher and lower temperature stress, and greater water stress than any other cultivars tested without dropping cyathias.

8. Merrimaker is similar to Glory and Super Rochford in breaking with new shoots after the terminal meristem has been removed. The Hegg and other Rochford types are generally considered as grassy and usually need some pruning. Stem caliber of Merrimaker is superior in comparison to the other cultivars noted.

9. Merrimaker roots faster and more uniform than Glory but is similar in propagation to the other cultivars, being well rooted in 14 days at 21° C.

10. Although the size, vigor, and growth habits are somewhat similar to the tetraploid cultivars Barbara Ecke Supreme and Indianapolis Red, Merrimaker is a diploid, being superior in every way to known poinsettias of commercial importance.

11. The apparent ease of flower initiation and the development of cyathia and bracts even under stress environments is of primary economic importance to both northern and deep south growers.

12. Merrimaker is more compact than Improved Rochford or Hegg Brilliant. Glory and Super Rochford are slightly more compact, and Glory is more upright in habit than Merrimaker.

13. In simulated shipping and storage tests in closed boxes for 3 to 10 days, Merrimaker showed no signs of epinasty (leaf petiole twisting), allegedly caused by traces of ethylene. Hegg and Rochford types and Paul Mikkelsen develop epinasty within 24–48 hours.

14. Merrimaker does not "split" or have the involucre separate as in Paul Mikkelsen, Hegg or Rochford types.

The accompanying colored photographic drawing illustrates the overall appearance of the new cultivar, with the colors being as true as possible to obtain in color reproductions of this type.

The following is a detailed description of the new cultivar based on plants produced under commercial practices in the greenhouses of Mikkelsens Inc., Ashtabula, Ohio, and photographed in December flowering. Color references are made to The Royal Horticultural Society Colour Chart except where general terms of ordinary dictionary significance are used.

Parentage: Controlled breeding by crossing Mikkelsen Seedling No. 72-143-2 (seed parent)×Mikkelsen Seedling No. 71-241-1 (pollen parent).

Propagation:

(A) *Type cutting.*—Stems 5 to 6 cm. in length.

(B) *Time to root.*—14 days at 21° C. summer; 18 days at 21° C. winter.

(C) *Rooting habit.*—Abundant and fibrous.

Plant description:

(A) *Form.*—Upright; when apical meristem is removed (pinching), leaving 5–6 nodes above the soil line of pot, generally 3 to 5 lateral shoots will emerge.

(B) *Growth habit.*—Strong stems that give excellent placement of bracts for flowering display. Growth is vigorous and under high humidity and reduced light the plants usually need applications of chemical growth retardants such as Cycocel. Involucre may become so heavy as to require staking of laterals to reduce breakage at node.

(C) *Foliage.*—Leaves are alternate and borne on 5–6 cm. long petioles that are purple-red in color. (1) Size: Mature leaves are 13–14.5 cm. long by 9–10 cm. wide at broadest area. (2) Quantity: Average for commercial poinsettias and variable in amount depending on cultural practices and growing environment. (3) Color: Mature plants characteristically have dark green foliage. New foliage, upper side, between 146B-C; under side between 146B-C. Old foliage, upper side 137A; under side 137C. (4) Shape: Ovate with leaf apices being ovate. (5) Texture: Upper side, glabrous with slightly rugose surface; under side rough with veins protruding. (6) Edge or margin: Slightly crenate. (7) Aspect: Foliage is nearly horizontal, tending to 45° below horizontal with maturation. No signs of epinasty from low levels of ethylene. (8) Insect and disease resistance: No evidence of mildew or botrytis problems to date. There is an apparent lack of preference of Merrimaker to white fly, as heavily infested adjacent cultivars did not cause buildup of egg masses on Merrimaker.

Flowering description:

(A) *Flowering habits.*—Earlier flowering than most commercial cultivars, apparently having a longer critical day length for flower initiation. Under controlled day length, development time is approximately 10 weeks. There will have to be considerable research into the matter of flower initiation under natural day lengths coupled with temperatures, in comparison to controlled day length prior to initiation and at initiation. It is very apparent that Merrimaker is flowering earlier than most commercial cultivars under *natural* day length in Ohio but takes approximately the same time to develop when tested under exact controlled day lengths with other commercial cultivars. This characteristic of earlier flower initiation is of commercial significance.

(B) *Borne.*—Involucre is almost flat with only slight reflexing. Cyathias stay closely clustered for considerable time without growing apart (splitting). Cyathias are very stress tolerant, remaining in the involucre for considerable time.

(C) *Quantity.*—Is highly dependent on cultural practices, and vary from a minimum of 8–10 to as many as 50. Cyathias continue to develop from November to April so there could be a total of more than 50.

(D) *Continuity.*—Flowering can be initiated any time of the year by controlled day length; cyathias will continue to initiate until day length is greater than approximately 13 hours and temperatures are not above 27° C.

(E) *Bracts.*—The last true leaves tend to become red. The primary bracts are ovate in shape and 15–16 cm. long and 8–9 cm. wide with petioles 2–2.5 cm. long. Secondary bracts are 8–10 cm. long and 4–5 cm. wide with petioles 1 to 1.5 cm. long as measured on a non-pinched plant. Dimensions will be somewhat smaller on pinched plants grown under the same cultural practices. The diameter of the bract head of a non-pinched plant is 35–40 cm. and on pinched plants 30–35 cm. Bract size can be quite variable depending on nutrition, temperatures, light, and other cultural practices. Number of bracts may vary up to 50 or more. Color: Upper side, young bracts, 45A-B; mature bracts close to 46B red but brighter or more vivid. Under side, young bracts red with green areas; mature bracts, 47B red.

(F) *Reproductive organs.*—(1) Stamens: Numerous, anther oblong, color yellow with red tint, filament red. (2) Pistils: Stigma forked, color reddish-purple, styles whitish-green. (3) Ovaries: 3 celled being 4 mm. long below receptive stigma, and yellow-green in color; 1 or 2 nectar cups are generally on each cyathia, yellow in color with tint of red. Nectar is usually readily available on maturing cyathias.

I claim:

1. A new and distinct cultivar of poinsettia plant named Merrimaker, as illustrated and described, and particularly characterized by its deep bright red colored bracts; dark green foliage; strong, vigorous, upright growth; early flowering; outstanding keeping quality, and by its commercially significant ability of being grown as a single stem or pinched plant.

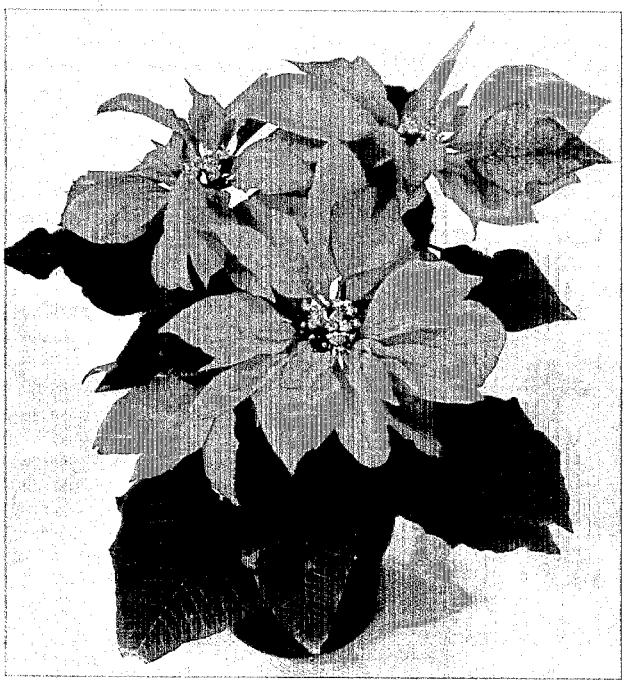

* * * * *